US008672967B2

United States Patent
DiMatteo et al.

(10) Patent No.: US 8,672,967 B2
(45) Date of Patent: Mar. 18, 2014

(54) PARTIAL THICKNESS ROTATOR CUFF REPAIR SYSTEM AND METHOD

(75) Inventors: Kristian DiMatteo, Waltham, MA (US); Gregory R. Whittaker, Stoneham, MA (US); Mehmet Ziya Sengun, Canton, MA (US)

(73) Assignee: DePuy Mitek, LLC, Raynham, MA (US)

( * ) Notice: Subject to any disclaimer, the term of this patent is extended or adjusted under 35 U.S.C. 154(b) by 970 days.

(21) Appl. No.: 12/609,122

(22) Filed: Oct. 30, 2009

(65) Prior Publication Data

US 2011/0106154 A1   May 5, 2011

(51) Int. Cl.
*A61B 17/04* (2006.01)

(52) U.S. Cl.
USPC ........................................................ 606/232

(58) Field of Classification Search
USPC ........................................................ 606/232
See application file for complete search history.

(56) References Cited

U.S. PATENT DOCUMENTS

| | | | | |
|---|---|---|---|---|
| 4,968,315 A | * | 11/1990 | Gatturna | 606/139 |
| 5,156,616 A | * | 10/1992 | Meadows et al. | 606/232 |
| 5,258,016 A | | 11/1993 | DiPoto | |
| 5,423,860 A | | 6/1995 | Lizardi | |
| 5,441,502 A | | 8/1995 | Bartlett | |
| 5,443,482 A | | 8/1995 | Stone | |
| 5,522,843 A | * | 6/1996 | Zang | 606/232 |
| 5,573,548 A | * | 11/1996 | Nazre et al. | 606/232 |
| 5,643,274 A | | 7/1997 | Sander | |
| 5,643,320 A | * | 7/1997 | Lower et al. | 606/232 |
| 5,690,676 A | | 11/1997 | DiPoto | |
| 5,690,677 A | | 11/1997 | Schmieding | |
| 5,733,307 A | | 3/1998 | Dinsdale | |
| 5,749,878 A | | 5/1998 | Bracy | |
| 5,814,051 A | | 9/1998 | Wenstrom, Jr. | |
| 5,814,070 A | | 9/1998 | Borzone | |
| 5,827,291 A | | 10/1998 | Fucci | |
| 5,840,078 A | | 11/1998 | Yerys | |
| 5,843,087 A | | 12/1998 | Jensen | |

(Continued)

FOREIGN PATENT DOCUMENTS

| | | |
|---|---|---|
| EP | 1884199 A1 | 2/2008 |
| WO | WO 2008/054814 A2 | 5/2008 |
| WO | WO 2009/113076 A1 | 9/2009 |

OTHER PUBLICATIONS

EP Search Report dated Feb. 1, 2011 for EP Appl. No. 10251875.0.

(Continued)

*Primary Examiner* — Corrine M McDermott
*Assistant Examiner* — Katelyn Bernier

(57) ABSTRACT

A suture anchor is disclosed which has an elongated body having a distal end, a proximal end and an exterior surface. An axially oriented bore extends into the body from the proximal end and a proximal portion of the bore has a plurality of abutment surfaces for engaging a tool. The bore includes one or more axially oriented suture passages leading to a suture attachment within the bore. A length of suture extends into the at least one suture passage from the body proximal end and extends to the suture attachment. A screw thread spirals about a portion of the exterior surface of the body adjacent the at least one suture passage. Between the bore and the exterior surface of the body the body has a wall thickness and wherein the suture passage comprises the area where the wall thickness goes to zero.

13 Claims, 5 Drawing Sheets

(56) References Cited

U.S. PATENT DOCUMENTS

| | | | |
|---|---|---|---|
| 5,941,882 A | 8/1999 | Jammet | |
| 5,948,000 A | 9/1999 | Larsen | |
| 5,948,001 A | 9/1999 | Larsen | |
| 5,951,559 A | 9/1999 | Burkhart | |
| 6,059,785 A | 5/2000 | Schavan | |
| 6,117,162 A | 9/2000 | Schmieding | |
| 6,214,031 B1 | 4/2001 | Schmieding | |
| 6,264,677 B1 | 7/2001 | Simon | |
| 6,508,830 B2* | 1/2003 | Steiner | 606/232 |
| 6,511,499 B2 | 1/2003 | Schmieding | |
| 6,652,563 B2 | 11/2003 | Dreyfuss | |
| 6,916,333 B2 | 7/2005 | Schmieding | |
| 7,195,634 B2 | 3/2007 | Schmieding | |
| 7,309,337 B2* | 12/2007 | Colleran et al. | 606/232 |
| 7,556,640 B2* | 7/2009 | Foerster | 606/326 |
| 7,695,494 B2* | 4/2010 | Foerster | 606/232 |
| 7,785,347 B2* | 8/2010 | Harvie et al. | 606/232 |
| 8,075,588 B2* | 12/2011 | Berberich et al. | 606/232 |
| 8,267,981 B2* | 9/2012 | Boock et al. | 606/308 |
| 2004/0106950 A1 | 6/2004 | Grafton | |
| 2005/0043735 A1 | 2/2005 | Ahmad | |
| 2005/0222618 A1 | 10/2005 | Dreyfuss | |
| 2005/0240199 A1 | 10/2005 | Martinek | |
| 2005/0283158 A1 | 12/2005 | West | |
| 2005/0288682 A1 | 12/2005 | Howe | |
| 2006/0122608 A1 | 6/2006 | Fallin | |
| 2006/0253119 A1 | 11/2006 | Berberich | |
| 2006/0276841 A1* | 12/2006 | Barbieri et al. | 606/232 |
| 2007/0032792 A1 | 2/2007 | Collin | |
| 2007/0198017 A1 | 8/2007 | Tschakaloff | |
| 2007/0213730 A1* | 9/2007 | Martinek et al. | 606/72 |
| 2007/0219557 A1* | 9/2007 | Bourque et al. | 606/72 |
| 2007/0219558 A1 | 9/2007 | Deutsch | |
| 2007/0225719 A1* | 9/2007 | Stone et al. | 606/72 |
| 2008/0033486 A1 | 2/2008 | Whittaker | |
| 2008/0058816 A1 | 3/2008 | Philippon | |
| 2008/0147063 A1 | 6/2008 | Cauldwell | |
| 2008/0147064 A1* | 6/2008 | Cauldwell et al. | 606/60 |
| 2008/0147119 A1 | 6/2008 | Cauldwell | |
| 2008/0275469 A1 | 11/2008 | Fanton | |
| 2008/0288069 A1 | 11/2008 | Wolf | |
| 2008/0306511 A1 | 12/2008 | Cooper | |
| 2009/0076544 A1 | 3/2009 | DiMatteo | |
| 2009/0076545 A1 | 3/2009 | DiMatteo | |

OTHER PUBLICATIONS

Millstein, Eric S. et al., Arthroscopic Management of Partial, Full-Thickness, and Complex Rotator Cuff Tears: Indication, Techniques, and Complications, Arthroscopy: The Journal of Arthroscopic and Related Surgery, Dec. 2003, pp. 189-199, vol. 19, No. 10.

Waibl, Bernhard et al., Partial-Thickness Articular Surface Supraspinatus Tears: A New Transtendon Suture Technique, Arthroscopy: The Journal of Arthroscopic and Related Surgery, Mar. 2005, pp. 376-381, vol. 21, No. 3.

Lo, Ian K.Y., et al., Transtendon Arthroscopic Repair of Partial-Thickness, Articular Surface Tears of the Rotator Cuff, Arthroscopy: The Journal of Arthroscopic and Related Surgery, Feb. 2004, pp. 214-220, vol. 20, No. 2.

Fox, Jeff A. et al., Pasta Lesion-Trans-Tendon Technique for Repair, Operative Techniques in Orthopaedics, 2002, pp. 191-196, vol. 12, No. 3.

Porat, Sharoun et al., Repair of partial thickness rotator cuff tears: A retrospective review with minimum two-year follow-up, J Shoulder Elbow Surg, 2008, pp. 727-721, vol. 17, No. 5.

Gonzalez-Lomas, Guillem et al., In situ transtendon repair outperforms tear completion and repair for partial articular-sided supraspinatus tendon tears, J Shoulder Elbow Surg, Sep./Oct. 2008, pp. 722-728, vol. 17, No. 5.

Brockmeier, Stephen F. et al., Arthroscopic Intratendinous Repair of the Delaminated Partial-Thickness Rotator Cuff Tear in Overhead Athletes, Arthroscopy: The Journal of Arthroscopic and Related Surgery, Aug. 2008, pp. 961-965, vol. 24, No. 8.

* cited by examiner

US 8,672,967 B2

PARTIAL THICKNESS ROTATOR CUFF REPAIR SYSTEM AND METHOD

BACKGROUND

The present application relates to systems and methods for performing a repair of a partial thickness rotator cuff tear.

A PASTA (Partial Articular Surface Tendon Avulsion) lesion in a rotator cuff of a shoulder can be particularly difficult to repair. The rotator cuff comprises a group of muscles which surround the shoulder and tendons which attach those muscles to the humeral head. The tendons have a footprint where they attach to the humeral head and in a PASTA lesion a portion of the tendon's footprint becomes detached from the humeral head. Such lesions are most commonly found on the supraspinatus tendon. One option for treatment is completion of the tear and repair using standard techniques for a full thickness tear. Preservation of the existing attachment is thus lost and the entire tendon must be reattached. A further option is to create an incision through the tendon and place a standard suture anchor therethrough. This creates significant trauma to the tendon.

SUMMARY OF THE INVENTION

The present invention provides systems and methods for repairing a PASTA lesion which provides advantages over current treatment options. A suture anchor according to the present invention comprises an elongated body having a distal end, a proximal end and an exterior surface. An axially oriented bore extends into the body from the proximal end and a proximal portion of the bore has a plurality of abutment surfaces for engaging a tool. The bore has at least one axially oriented suture passage. A suture attachment is associated with the bore. A screw thread extends about a portion of the exterior surface of the body adjacent the at least one suture passage. The body has a wall thickness between the bore and the exterior surface of the body, the suture passage comprising an area where the wall thickness goes to zero.

Preferably, the wall thickness is zero along substantially an entire length of the bore.

Preferably, the abutment surfaces form a tool receiving recess and wherein the at least one suture passage comprises a first suture passage on a first side of the tool receiving recess and a second suture passage on a second side of the tool receiving recess. A length of suture can pass down the first suture passage to the suture attachment and then back out the second suture passage. Preferably, the tool receiving recess extends substantially from the body proximal end to the suture attachment providing good purchase for the tool and reducing stress upon the anchor body during tool use. In one embodiment, the threads have a maximum outer diameter less than 4 mm and wherein the suture is of gauge #2 or lower. Preferably, the threads have a maximum outer diameter less than 3.5 mm, and more preferably, a maximum outer diameter of 2.8 mm.

Preferably, the suture anchor has a pullout resistance of at least 25 lbs.

In one embodiment, the body is formed of a bioabsorbable polymer and in an alternative embodiment of Titanium.

Preferably, the suture attachment comprises a cross member disposed within the bore allowing sliding of the suture therethrough.

Preferably, the suture anchor further comprises a driver inserted into a tool receiving recess formed between the abutment surfaces, the driver comprising complementary surfaces in engagement with the abutment surfaces whereby to apply torque to the suture anchor body. Preferably, the driver further comprises at least one suture receiving groove adjacent the complementary surfaces and in registry with the at least one suture passage in the anchor body.

A method according to the present invention provides for performing a partial thickness rotator cuff repair. The method includes the steps of: inserting a first suture anchor having a maximum diameter of 4.0 mm through a tendon of the rotator cuff and anchoring it into the humerus; inserting a second suture anchor into the humerus; passing a first length of suture from the first suture anchor through the tendon and to the second suture anchor whereby to hold the tendon to the humerus.

In one embodiment of the method, the first suture anchor is formed of a bioabsorbable material. Preferably, after insertion, the first suture anchor is not proud of a surface of the humerus. Preferably, the method further comprises the step of passing a second length of suture from the first suture anchor and through the tendon. It can further comprise anchoring a third suture anchor into the humerus and passing the second suture to the third suture anchor.

Preferably, the first suture anchor has a maximum diameter of 3.5 mm, and more preferably 2.8 mm.

DETAILED DESCRIPTION

Figure 1:
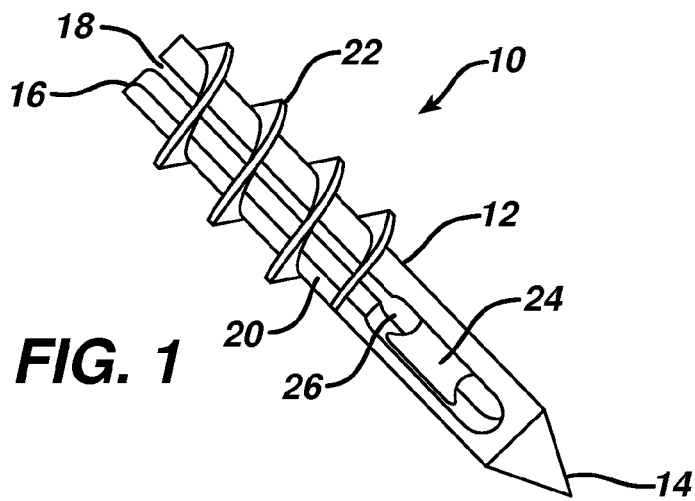
FIG. 1 is a perspective view of a suture anchor according to the present invention.

FIG. 1 depicts a suture anchor 10 according to the present invention. It comprises an elongated body 12 having a pointed distal tip 14 and a proximal end 16. An axial passageway 18 extends into the body 12 from the proximal end 16. The passageway 18 is open along its sides 20. A thread 22 encircles the body 12. A suture bridge 24 spans the passageway 18 laterally at a distal portion 26 thereof.

Figure 2:
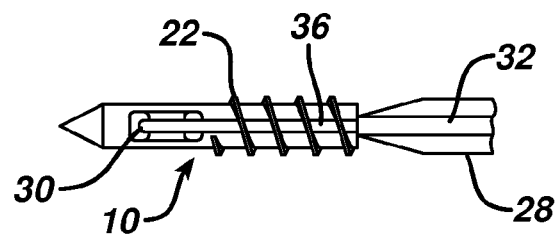
FIG. 2 is a side elevation view of the suture anchor of FIG. 1 loaded onto a driver.
Figure 3:
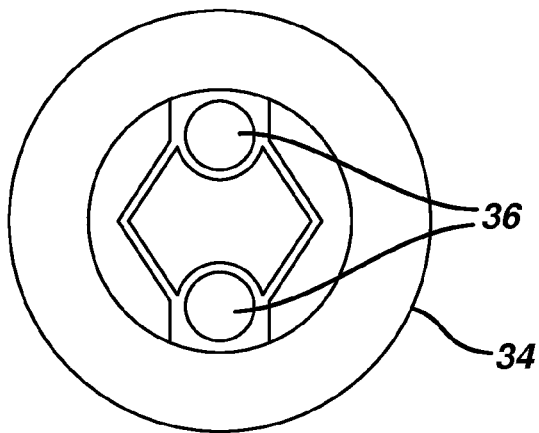
FIG. 3 is a top plan view of the suture anchor of FIG. 1.

Turning also now to FIGS. 2 and 3, an inserter 28 fits into the passageway 18. A length of suture 30 passes around the suture bridge 24 and is received within longitudinal grooves 32 on the inserter 28. As best seen in FIG. 3, the cross-sectional shape of the passageway 18 at the proximal end 16 is essentially a hexagon 34 with a pair of suture passages 36 on opposite corners thereof. The suture passages 36 lead to either side of the suture bridge 24. The inserter 28 has a complimentary shape to fit within the hexagon 34 with its grooves 32 in alignment with the suture passages 36 on the anchor 10.

The suture anchor 10 as shown with the suture passages 36 penetrating the body 12 to leave the passageway 18 open except for the thread 22 minimizes its cross section to provide the least trauma to soft tissue through which it will pass while still having sufficient mechanical strength for the driver 28 to drive it into bone. Where additional fixation strength within the bone may be required the cross section of the anchor 10 could be enlarged, in which case the suture passages 36 need then not necessarily penetrate the body 12 laterally. The anchor 10 can be formed of any suitable biocompatible material such as stainless steel, titanium, cobalt chrome, PEEK (polyaryletheretherketone), other biocompatible polymers, polymer-ceramic composites, bioabsorbable polymers and the like.

Figure 4:
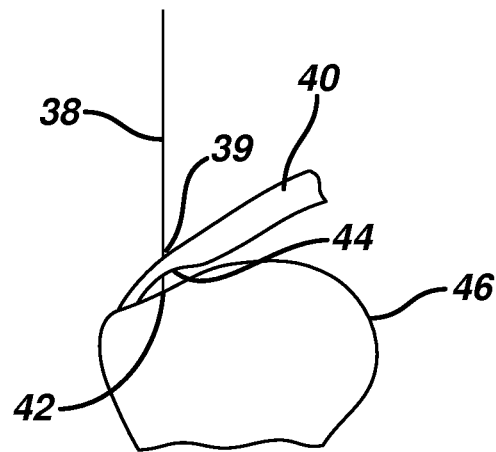
FIG. 4. is a side elevation view of a humerus and associated rotator cuff tendon suffering a PASTA lesion showing a K wire being inserted through the tendon to a desired location for placing a suture anchor.

FIGS. 4 to 10 illustrate a procedure to repair a PASTA lesion using the suture anchor 10 of FIG. 1. As seen in FIG. 4, either percutaneously or arthroscopically, a Kirschner wire (K wire) 38 is inserted at a first location 39 through a tendon 40 of a rotator cuff to a desired anchor site 42 beneath its attachment footprint 44 and positioned upon an associated humeral head 46. The K wire 38 can be tapped in or merely positioned at the site 42. To ease manipulation of the K wire 38 it is preferably textured on its outer surface and may be provided with a removable proximal handle (not shown). This site 42 on the humeral head 46 is where the suture anchor 10 (see FIG. 1) will be implanted.

Figure 5:
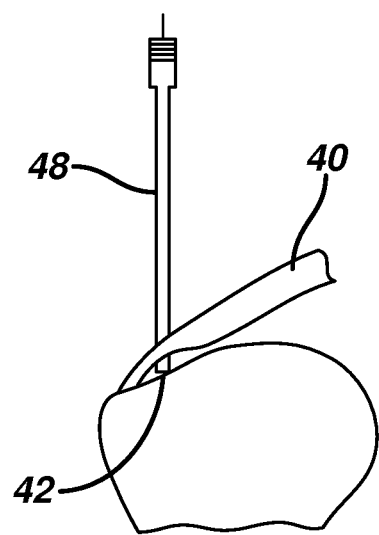
FIG. 5. is a side elevation view of the tendon of FIG. 4 showing a cannula system being passed through the tendon over the K wire.
Figure 6:
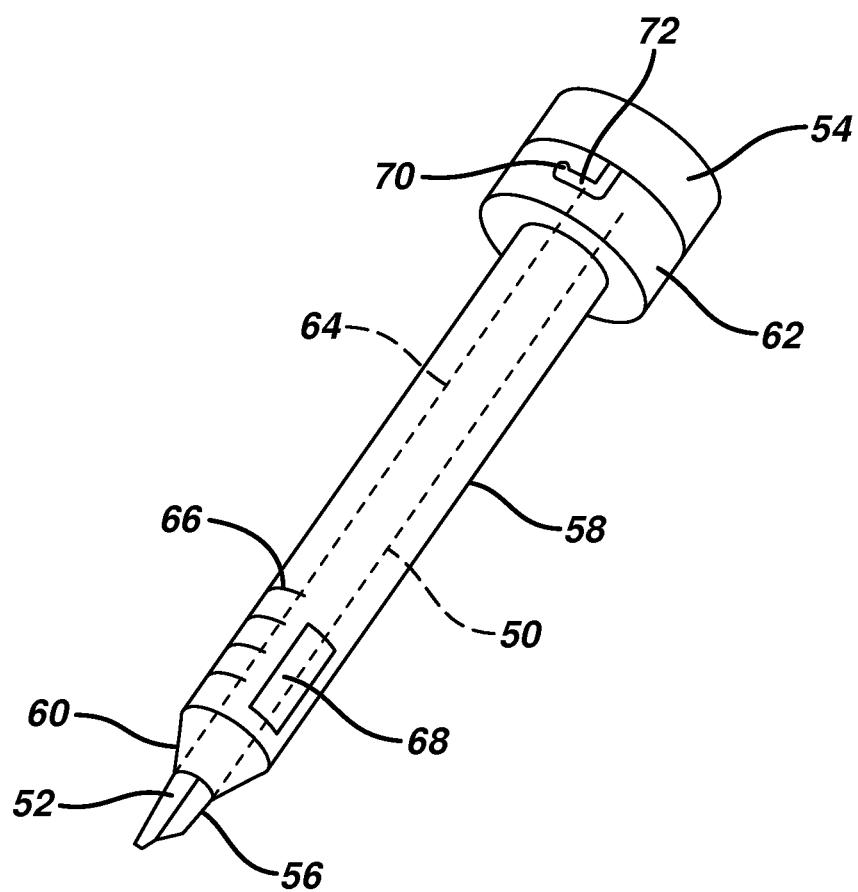
FIG. 6 is a perspective view of the cannula system of FIG. 5.

As seen in FIG. 5, a cannula system 48 is passed over the K wire 38 and through the tendon 40 to the site 42. FIG. 6 shows the cannula 48 in more detail. It comprises an inner cannula 50 having a sharp distal tip 52, proximal handle 54 and a lumen 56 therethrough. The inner cannula 50 fits within an outer cannula 58 which has a distal end 60, proximal handle 62 and lumen 64 therethrough. The distal tip 52 of the inner cannula 50 extends slightly beyond the distal end 60 of the outer cannula 58 and the distal end 60 is tapered so that rather than core through the tendon 40 the distal tip 52 creates a small hole and the tapering on the distal tip 52 and distal end 60 allow the cannula system 48 to push aside the tissue and create the smallest hole through the tendon 40 with the least damage thereto. Prior cannulas were inserted through a slit cut into the tissue. The cannula system 48 dilates the tissue gently to minimize trauma to the tissue. The outer cannula 58 has lines 66 which provide a visual indication of depth penetration and also a visualization window 68 which aids in anchor insertion and assessment of appropriate depth into the bone. To prevent slippage of the inner cannula 50 relative to the outer cannula 58 during insertion so provision is preferably provided to help keep them together. Shown are an interlocking nub 70 and groove 72, but other options such as a friction fit, threading, magnets etc. could be employed.

Figure 7:
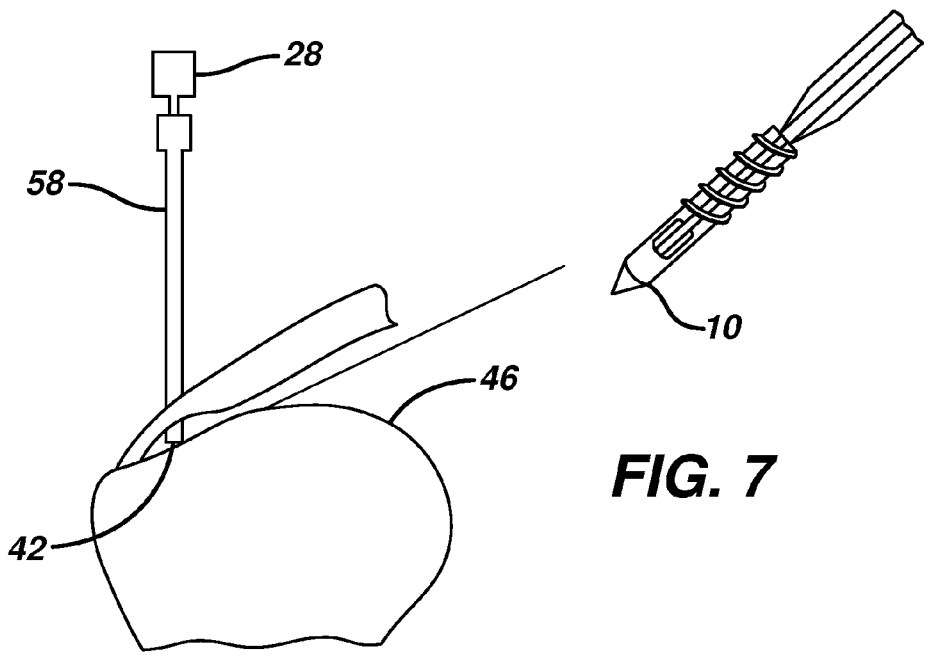
FIG. 7 is a side elevation view of the tendon of FIG. 4 a suture anchor loaded onto a driver being passed therethrough via an outer portion of the cannula system.
Figure 8:
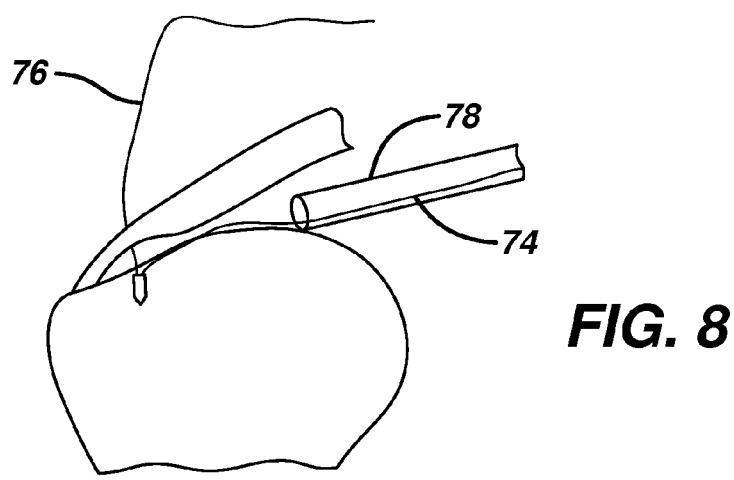
FIG. 8 is a side elevation view of the tendon of FIG. 4 showing the suture anchor implanted into the humerus beneath the tendon and a limb of suture passing from the suture anchor out of an anterior cannula.

As seen in FIG. 7, in preparation for insertion of the anchor 10, the K wire 38 and inner cannula 50 are removed leaving the outer cannula 58 positioned at the anchor site 42. The suture anchor 10 is preloaded onto the inserter 28, with the suture 30 in place around the suture bridge 24 and passing through the suture passages 36 and grooves 32 (see FIG. 2), is passed down through the outer cannula lumen 60 to the anchor site 42 and is then driven into the humeral head 46. If the anchor 10 is formed of a biocompatible metal such as stainless steel or titanium it can be simply twisted in via the inserter 28. If instead it is formed of a bioabsorbable polymer or other material having less strength a pilot hole should be prepared such as with a drill, tap or awl, at the site 42 through the cannula 46 prior to inserting the anchor 10 through the lumen 60. The inserter 28 and outer cannula 58 can then be removed leaving first and second suture limbs, 74 and 76 respectively, passed up through the tendon 40 at the first location 39 through which the cannula 48 had passed. As seen in FIG. 8, the first suture limb 74 is then retrieved through an auxiliary cannula 78 such as via a grasper (not shown).

Figure 9:
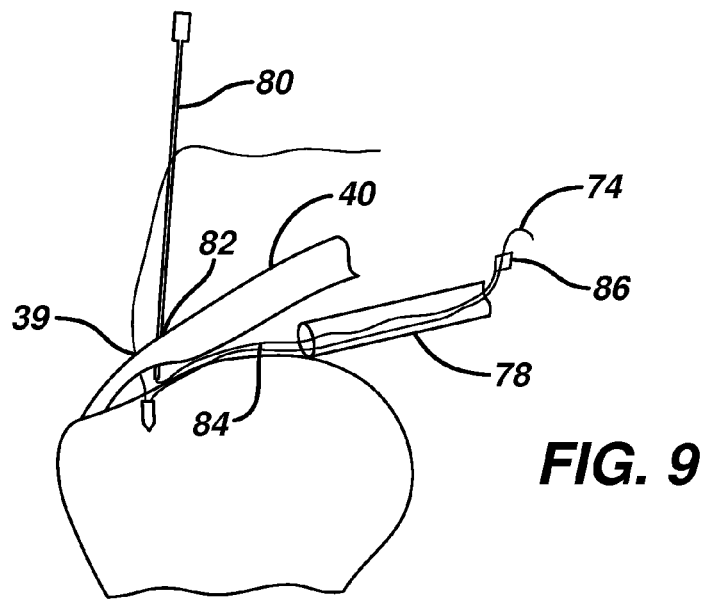
FIG. 9 is a side elevation of the tendon of FIG. 4 showing a spinal needle passed through a location on the tendon and a suture retriever being passed through the spinal needle and out of the anterior cannula.
Figure 10:
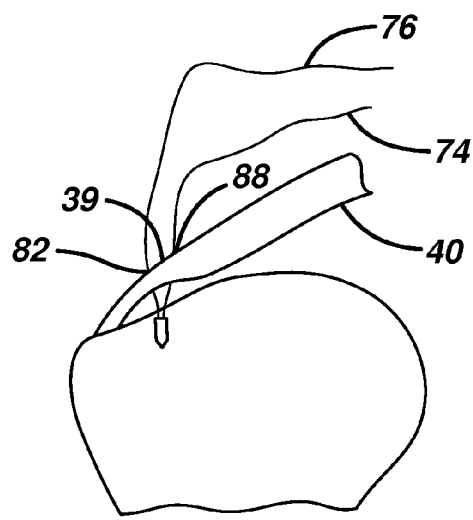
FIG. 10 is a side elevation of the tendon of FIG. 4 showing both suture limbs passed from the suture anchor and through the tendon at different locations.
Figure 11:
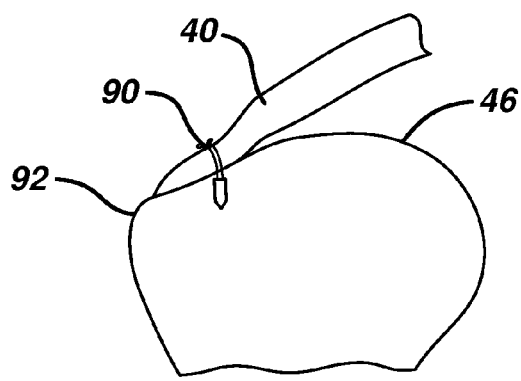
FIG. 11 is a side elevation of the tendon of FIG. 4 showing the suture limbs knotted together to compress the tendon to the humerus thus effecting repair of the PASTA lesion.

As seen in FIG. 9 a spinal needle 80 is passed through the tendon 40 at a second location 82 spaced apart from the first location 39. A flexible wire suture capture device 84 having a suture capture loop 86 (such as a Chia Percpasser available from DePuy Mitek, Inc. of Raynham, Mass.) is passed through the spinal needle 80 and retrieved out through the auxiliary cannula 78 so that the first suture limb 74 can be threaded through the suture capture loop 86. When the spinal needle 80 and suture capture device 84 are pulled back through the skin this pulls the first suture limb 74 through the tendon 40 at the second location 82. For a quick procedure, the first and second suture limbs 74 and 76 could now be knotted together tying down the tendon 40. However, it is preferable to repeat the procedure of FIGS. 8 and 9 with the second suture limb 76 to pass it through the tendon 40 at a third location 88 on an opposite side of the first location 39 as shown in FIG. 10. To ease in knot tying both suture limbs 74 and 76 are preferably pulled out through a single portal such as the auxiliary cannula 78 or other portal through the skin. A knot 90 can then be tied and pushed down to tightly secure the tendon 40 to the humeral head 46 as shown in FIG. 11. By passing the suture limbs 74 and 76 through the tendon 40 at locations 82 and 88 on opposite sides of the first location 39 and defect caused at that location via the passing of the cannula system 48 will be naturally pulled together when the knot 90 is tightened.

Depending upon the extent of the PASTA lesion it may be desirable to place more than one suture anchor 10 beneath the tendon 40. In such case the suture limbs therefrom can be tied together. It would still be preferable to pass them through the tendon at separate locations as illustrated in FIGS. 9 and 10 prior to tying them together, preferably in a mattress pattern. Also, a repair could be fashioned employing one or more knotless suture anchors (not shown) such as disclosed in U.S. Published Application No. 2008/0033486, incorporated herein by reference placed at a location 92 laterally of the tendon 40 and wherein the suture limbs 74 and 76 from the one or more anchors 10 can be passed in a dual row procedure, preferably also employing a mattress pattern. If a lateral anchor is employed, one such method is to put the a pair of present suture anchors 10 anterior and posterior and have one limb 74 from each tied to each other and the other limbs 76 spanned to the lateral anchor (preferably knotless) such that it forms a triangle.

The suture anchor 10 and cannula system 48 may also be used to effect repair of a SLAP (Superior labral tear from Anterior to Posterior) lesion. Typically a much larger traditional cannula (7-8 mm) is placed thru the rotator cuff to access the superior labrum for a SLAP repair. The present cannula system is much smaller and also due to its tendency to dilate the tissue rather than be inserted through a large slit would inflict less trauma to the rotator cuff. Such a procedure may be as follows: insert the K wire 38, and then the cannula system 48 in the fashion heretofore described through the rotator interval; drill a hole in the glenoid rim; insert the anchor 10; remove the cannula system 48; pass suture through the labrum using a suture shuttle; and tie knots.

While the invention has been particularly described in connection with specific embodiments thereof, it is to be understood that this is by way of illustration and not of limitation, and that the scope of the appended claims should be construed as broadly as the prior art will permit.

What is claimed is:

1. A suture anchor comprising:
   an elongated body having a distal end, a proximal end and an exterior surface;
   an axially oriented bore into the body from the proximal end;
   a proximal portion of the bore having a plurality of abutment surfaces for engaging a tool;
   the bore comprising at least one axially oriented suture passage;
   a suture attachment associated with the bore;
   a screw thread about a portion of the exterior surface of the body adjacent the at least one suture passage; and
   the body having a wall thickness between the bore and the exterior surface of the body, the suture passage comprising an area where the wall thickness goes to zero between the screw thread and the bore.

2. A suture anchor according to claim 1 wherein the wall thickness is zero along an entire length of the bore.

3. A suture anchor according to claim 1 wherein the abutment surfaces form a tool receiving recess and wherein the at least one suture passage comprises a first suture passage on a first side of the tool receiving recess and a second suture passage on a second side of the tool receiving recess.

4. A suture anchor according to claim 3 wherein a length of suture passes down the first suture passage to the suture attachment and then back out the second suture passage.

5. A suture anchor according to claim 4 wherein the screw thread has a maximum outer diameter less than 4 mm and wherein the suture is of gauge #2 or lower.

6. A suture anchor according to claim 5 wherein the screw thread has a maximum outer diameter less than 3.5 mm.

7. A suture anchor according to claim 6 wherein the screw thread has a maximum outer diameter of 2.8 mm.

8. A suture anchor according to claim 7 having a pullout resistance of at least 25 lbs.

9. A suture anchor according to claim 1 wherein the body is formed of a bioabsorbable polymer.

10. A suture anchor according to claim 1 wherein the body is formed of titanium.

11. A suture anchor according to claim 1 wherein the suture attachment comprises a cross member disposed within the bore.

12. A suture anchor according to claim 1 and further comprising a driver inserted into a tool receiving recess formed between the abutment surfaces, the driver comprising complementary surfaces in engagement with the abutment surfaces whereby to apply torque to the suture anchor body.

13. A suture anchor according to claim 12 wherein the driver further comprises at least one suture receiving groove adjacent the complementary surfaces and in registry with the at least one suture passage in the anchor body.

* * * * *